United States Patent [19]

Pawloski et al.

[11] 4,450,280

[45] May 22, 1984

[54] PHOSPHOROUS-CONTAINING POLYETHER POLYOLS

[75] Inventors: Chester E. Pawloski, Bay City; Sally P. Ginter, Sanford, both of Mich.

[73] Assignee: The Dow Chemical Company, Midland, Mich.

[21] Appl. No.: 354,567

[22] Filed: Mar. 4, 1982

[51] Int. Cl.$^3$ ...................... C07F 9/40; C07D 317/24
[52] U.S. Cl. .................................... 549/221; 260/928; 260/932; 260/953
[58] Field of Search ...................... 260/953, 928, 932; 549/221

[56] References Cited

U.S. PATENT DOCUMENTS

| | | | |
|---|---|---|---|
| 3,094,549 | 6/1963 | Gurgiolo | 260/953 |
| 3,393,254 | 7/1968 | Hartman et al. | 260/953 |
| 4,365,026 | 12/1982 | Pawloski et al. | 521/168 |

Primary Examiner—Anton H. Sutto
Attorney, Agent, or Firm—Douglas N. Deline

[57] ABSTRACT

Phosphorus-containing polyether polyols are prepared by reacting phosphorus-containing acids with tertiary alkyl glycidyl ether and subsequently dealkylating the tertiary alkyl functionality.

7 Claims, No Drawings

PHOSPHOROUS-CONTAINING POLYETHER POLYOLS

BACKGROUND OF THE INVENTION

Polyurethanes, particularly polyurethane foams, have many uses in which fire retardancy is an important and highly desirable property. It is well-known to impart some degree of fire retardancy to polyurethane foams by incorporating into such foams a fire-retarding agent such as phosphorus. Most conveniently, the phosphorus is introduced as one component of the reaction medium, preferably the polyol reactant thereby simplifying the procedure and equipment necessary in order to produce the resulting polyurethane, but additionally providing a polyurethane wherein the phosphorus component is integrally bonded to the polymer and not merely physically incorporated.

It is already known to prepare phosphorus-containing polyether polyols by reaction of phosphoric acid with an alkylene oxide. For example, in U.S. Pat. No. 3,639,543, phosphoric acid and derivatives thereof were reacted with alkylene oxides such as ethylene oxide, propylene oxide, etc. Polyols prepared in this manner contain no added hydroxyl functionality and consequently are limited to the functionality of the initiator. Furthermore, these phosphorus-containing polyether polyols of the prior art have the inherent disadvantage of providing only terminal hydroxyl functionality, e.g., hydroxyl functionality only at the end of the polymer chain not pendant from the backbone. Attempts at providing other than terminal hydroxyl functionality, e.g., by reaction of glycidol with phosphoric acid, result in high molecular weight cross-linked residues due to reaction of the hydroxyl functionality.

Primary hydroxyl-containing polyether polyols made by reaction of tertiary butyl glycidyl ether alone or in combination with other alkylene oxides and suitable initiators followed by dealkylation are also known. In British Patent specification No. 1,267,259, tertiary butyl glycidyl ether is reacted with compounds or mixtures of compounds having one active hydrogen atom selected from alcohols, polyols, halogenated alcohols, water, thiols, mercapto-alkanols and phenols. Catalysts for the reaction include Lewis acids such as $BF_3$, $SnCl_4$, $SbCl_5$, etc.

In U.S. Pat. No. 4,086,194, halogen- and hydroxyl-containing polymers are prepared by reaction of halides of alkyl and aryl phosphonic acids with glycidol. The compound was found to be a highly viscous material, probably due to reaction of hydroxyl functionality during the reaction as previously discussed. The product was added to a conventional polyol diluent prior to making of the polyurethane.

It is seen that conventional phosphorus-containing polyols have not been satisfactory. It is desirable to prepare a phosphorus-containing polyol containing pendant primary hydroxyl functionality thereby providing phosphorus-containing polyols of low hydroxyl number.

It is further desirable to prepare phosphorus-containing polyols that are not overly viscous liquids or intractable solids but instead are free-flowing liquids that may be used in the preparation of polyurethanes without the addition of a liquid diluent.

It is further desirable to provide phosphorus-containing polyols having high phosphorus and halogen content useful in preparing polyurethanes having increased flame retardancy.

SUMMARY OF THE INVENTION

According to the invention, these and other desirable objects are obtained by phosphorus-containing polyether polyols corresponding to the formula:

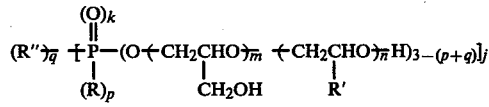

wherein:
R is a monovalent moiety having up to 6 carbons selected from the group consisting of alkyl, phenyl, haloalkyl, halophenyl, alkoxy and haloalkoxy;
R' is $C_{1-6}$ alkyl, $C_{1-6}$ haloalkyl, phenyl, halophenyl, tertiary alkoxymethyl, phenoxymethyl, halophenoxymethyl, or

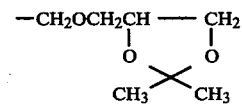

R'' is a moiety of valence j having up to 10 carbons selected from the group consisting of R, alkanediyl, alkanetriyl, alkanetetryl, alkenylene, alkylenedioxy and halo-, haloalkyl-, phenyl- or halophenyl-substituted derivatives thereof; j is an integer from 1 to 4
k is zero or one;
m is a positive rational number less than about 25;
n is a rational number from zero to about 25; and
p and q are integers independently equal to either zero or 1.

By the term haloalkyl, halophenyl, haloalkoxy and halophenoxy are included mono- and polyfluoro-, chloro-, bromo- and iodo-substituted alkyl, phenyl, alkoxy and phenoxy groups. Preferred are mono or poly brominated or chlorinated substituents. Most preferably R is haloalkyl, particularly chloromethyl or bromomethyl.

The phosphorus-containing polyether polyols are useful in the formation of polyurethane products, particularly polyurethane foams possessing reduced tendency to burn.

DETAILED DESCRIPTION OF THE INVENTION

The compounds of the instant invention are esters of phosphorus-containing acids formed by reacting a suitable phosphorus-containing acid with a tertiary alkyl glycidyl ether alone or in combination with other alkylene oxides or epoxides followed by dealkylation according to known techniques. As a practical matter, tertiary butyl glycidyl ether is the tertiary alkyl glycidyl ether of primary interest.

Suitable phosphorus-containing acids are those acids of the formula:

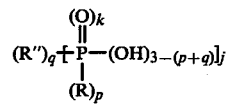

wherein R, R", j, k, p and q are as previously defined. Also suitable are acid precursors of the above acids, for example, phosphorus pentoxide.

Suitable phosphorus acids corresponding to the above formulas include the well-known phosphoric acid and phosphonic, phosphinic, phosphorous or phosphinous acids as defined in U.S. Pat. No. 2,856,369, which teaching is incorporated herein by reference.

Included as bridged phosphorus acids are free acids prepared, for example, by the technique of U.S. Pat. No. 3,471,552 which teaching is also incorporated herein in its entirety by reference. Additional compounds of this sort are easily prepared by other well-known techniques, for example, by reaction of phosphorus pentoxide with a diol or an epoxide including halogenated epoxides. The latter reaction is further described in more detail in Example 8 herein.

The phosphorus-containing acid is reacted with tertiary alkyl glycidyl ether alone or in combination with other alkylene oxides or epoxides either concurrently or serially to produce homopolymers or copolymers having random or blocked ether functionality or combinations thereof. The alkylene oxides or epoxides that may optionally be coreacted with the tertiary alkyl glycidyl ether include, for example, ethylene oxide, propylene oxide, epichlorohydrin, epibromohydrin, trihalo butylene oxides, 2,2-dimethyl-1,3-dioxolan-5-methyl glycidyl ether, phenyl glycidyl ether, halogenated phenyl glycidyl ethers, etc.

The reaction is conducted in a well-known manner merely by contacting the reactants optionally at elevated temperatures. A catalyst may be employed if desired. Suitable catalysts include Lewis acids such as boron trifluoride etherate, etc.

Control in placement of the ether moieties in a given reaction cannot be carefully controlled. The reaction product, therefore, comprises a mixture of esters having varying numbers of glycidyl ether remnants in each individual molecule. On a gross basis, however, the empirical formula provided defines the formula of the compounds produced wherein m and n are determined by the total number of moles of tertiary alkyl glycidyl ether, alkylene oxide or other epoxide, reacted respectively along with the number of moles of phosphorus-containing acid and the number of reactive hydroxyl sites in each acid molecule.

Dealkylation of the tertiary alkyl functionality of the resulting compounds is accomplished according to well-known techniques. For example, heating to temperatures of about 120° C. or greater optionally in the presence of a strong acid or ion-exchange resin in the acid form for a time sufficient to achieve the desired degree of dealkylation. The progress of the dealkylation may be conveniently monitored by nuclear magnetic resonance spectroscopy.

As previously mentioned, one advantage of the present invented phosphorus-containing polyether polyols is the lack of cross-linking and subsequent thickening of the resulting product. Preferred according to the present invention are polyols having viscosities (as measured directly at 25° C. by a Brookfield viscosity meter) of less than 500,000 cps and most preferably less than 50,000 cps.

The phosphorus-containing polyether polyols of the invention preferably have theoretical molecular weights in the range from about 225–2500 with phosphorus contents of from about 2 percent to about 10 percent by weight, halogen content from about 10 percent to about 40 percent by weight, and from about 3 to about 6 hydroxyls per molecule.

Most preferred ranges are:

| | |
|---|---|
| theoretical molecular weight | 400–800 |
| phosphorus content by weight | 5–10% |
| halogen content by weight | 20–30% |
| hydroxyl content per molecule | 3–5 |

SPECIFIC EMBODIMENTS

Having described the invention the following examples are provided as further illustrative and are not to be construed as limiting.

EXAMPLE 1

Into a one-liter three-necked flask were placed 98 g of 85 percent phosphoric acid (1.0 mole), 200 ml of methylene chloride and 2 ml of boron trifluoride etherate. This mixture was stirred while a solution of 185 g epichlorohydrin (2.0 moles) in 130 g of tertiary butyl glycidyl ether (t-BGE) (1.0 mole) was added dropwise at a rate to maintain a gentle reflux. When this addition was complete, another ml of boron trifluoride etherate and another 185 g of epichlorohydrin (2.0 moles) were added. After this addition, the mixture was refluxed until reaction was complete. The flask was equipped with a short distillation column and slowly heated to 130° C.–135° C. while low boilers distilled off. Heating was continued until dealkylation of the t-butoxy group was complete by nuclear magnetic resonance spectra. The mixture was allowed to cool to 85° C. and 10 g of sodium carbonate were added. The mixture was filtered and gave 519 g of a light oil, 96 percent yield (23,250 cps Brookfield viscosity).

The polymers prepared corresponded to the formula:

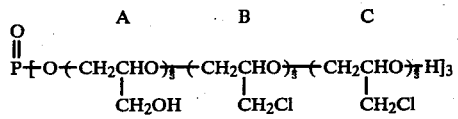

in which each polyether chain contained an initial random mixture of chloromethyl ethyleneoxy and hydroxymethyl ethyleneoxy moieties (units A and B) followed by terminal block functionality which was chloromethyl ethyleneoxy (unit C).

EXAMPLE 2

The reaction conditions of Example 1 were substantially repeated employing the following components in the order listed:

85% phosphoric acid (200 g, 2.0 moles)
500 ml methylene chloride
a solution of 370 g epichlorohydrin (4.0 moles) and t-BGE (2.0 moles)
boron trifluoride etherate (1 ml)
370 g epichlorohydrin (4.0 moles)
88 g ethylene oxide (2.0 moles)+boron trifluoride etherate The product was light amber colored oil (1160 g), 99 percent yield (12,200 cps Brookfield viscosity).

The polymer thus prepared corresponded to the formula:

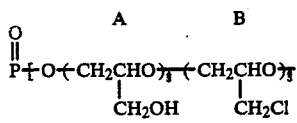

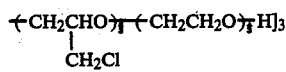

wherein repeating units A and B were in random order and C and D were in block copolymer form, and the combination of random units A and B were in block form with units C and D.

EXAMPLE 3

Into a five-liter flask were placed 300 g of 85 percent phosphoric acid (3.0 mole), 600 ml of methylene chloride and 1 ml of boron trifluoride etherate. This mixture was stirred while a solution of 550 g of epichlorohydrin (6.0 moles) in 390 g of t-BGE (3.0 mole) was added dropwise at a rate to maintain a gentle reflux. After this addition, another ml of boron trifluoride etherate and 832 g (9.0 moles) of epichlorohydrin were added dropwise at reflux temperatures. After this addition, the mixture was refluxed until the reaction was complete. The flask was equipped with a short distillation column and slowly heated to 110° C. This temperature was maintained until the dealkylation of the t-butoxy groups was complete by nuclear magnetic resonance spectra. The mixture was stirred, filtered and distilled under reduced pressure to remove the solvent to give 1900 g of an oil, 100 percent yield (18,200 cps Brookfield viscosity).

EXAMPLE 4

Phosphorus Acid

Into a one-liter flask was placed 82 g of 98 percent phosphorus acid (1.0 mole) and 500 ml of methylene chloride. This mixture was stirred while a solution of 185 g epichlorohydrin (2.0 moles) in 130 g t-BGE (1.0 mole) was added dropwise. The reaction was very slow so 1 ml boron trifluoride etherate was added. The reaction was then exothermic. After this addition, the mixture was stirred for 30 minutes and another ml of boron trifluoride etherate and a solution of 185 g epichlorohydrin (2.0 moles) in 58 g of propylene oxide were added dropwise. The mixture was then refluxed until unreacted propylene oxide moieties were no longer detected. 2 g Of p-toluenesulfonic acid hydrate dealkylation catalyst were added. The mixture was heated to 140° C. until dealkylation was complete by nuclear magnetic resonance spectra. The product was an oil (564 g), 97 percent yield (12,800 cps Brookfield viscosity).

The polymer thus prepared corresponded to the formula:

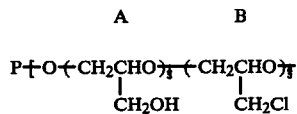

-continued

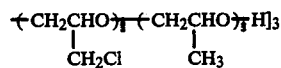

wherein repeating units A and B were in random order and units C and D were in random order, but the combination of units A and B and the combination of units C and D were in blocked order.

EXAMPLE 5

Phenyl Phosphonic Acid

The reaction conditions of Example 4 were substantially repeated employing the following ingredients in the order shown:

phenyl phosphonic acid (80 g, 0.5 mole)
400 ml methylene chloride
boron trifluoride etherate (1 ml)
92.5 g epichlorohydrin (1.0 mole)+t-BGE (65 g, 0.5 mole)
boron trifluoride etherate (1 ml)
92.5 g epichlorohydrin (1.0 mole)
p-toluenesulfonic acid (1 g)

The product obtained was a dark oil (300 g), 99 percent yield (17,810 cps Brookfield viscosity).

The polymer thus prepared corresponded to the formula:

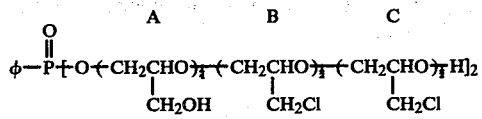

wherein units A and B singly were randomly ordered, but collectively were in block copolymeric order with unit C.

EXAMPLE 6

Trichloromethylphosphonic Acid

Into a two-liter three-necked flask were placed 60 g of trichloromethylphosphonic acid (0.3 mole), 600 ml of methylene chloride and 6 ml of boron trifluoride etherate. This mixture was stirred while a solution of 333 g of epichlorohydrin (3.6 moles) and 78 g of t-BGE (0.6 mole) was added dropwise at a rate to maintain a gentle reflux. After this addition, the mixture was refluxed until reaction was complete. The flask was equipped with a short distillation column and the low boilers removed by distillation until 130° C. was obtained. Heating was continued until dealkylation of the t-butoxy groups was complete by nuclear magnetic resonance spectra. The product was taken up in 800 ml methylene chloride and stirred with 200 ml of a 10 percent NaOH water solution. The product layer was separated, dried over sodium sulfate, filtered and distilled to give 379 g of an oil, 87 percent yield (62,000 cps Brookfield viscosity).

The polymer thus formed corresponded to the formula:

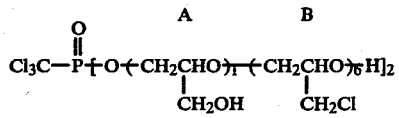

wherein units A and B were in random order.

EXAMPLE 7

Phosphorus Pentoxide Derivatives

The reaction conditions of Example 6 were substantially repeated excepting that a mixture of monomethyl and dimethyl esters of phosphoric acid was first prepared by reaction of methanol with phosphorus pentoxide. The following ingredients were combined and reacted in the order stated:
- phosphorus pentoxide (142 g, 1.0 mole)
- 750 ml methylene chloride
- 96 g methanol (3.0 moles)
- 130 g t-BGE (1.0 mole) + epichlorohydrin (185 g, 2.0 moles)
- boron trifluoride etherate (1 ml)
- 185 g epichlorohydrin (2.0 moles)

The product obtained was a dark oil (630 g), 92 percent yield (15,000 cps Brookfield viscosity).

The polymers thus formed corresponded to the following formulas:

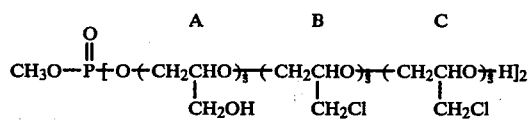

and

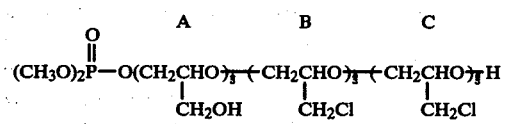

wherein polymeric units A and B were in random order, but unit C was in block order.

EXAMPLE 8

A bridged phosphorus acid ester was prepared by reacting phosphorus pentoxide with water and epichlorohydrin. Accordingly, the following ingredients were combined and reacted in the order provided substantially according to the reaction procedure of Example 7.
- phosphorus pentoxide (142 g, 1.0 mole)
- 100 ml 1,4-dioxane (solvent)
- 750 ml methylene chloride
- a solution of water (18 g) and 1,4-dioxane (100 ml)
- 93 g epichlorohydrin (1.0 mole)
- boron trifluoride etherate (1 ml)
- 185 g epichlorohydrin (2.0 moles) + t-BGE (130 g, 1.0 mole)
- boron trifluoride etherate (1 ml)
- 185 g epichlorohydrin (2.0 moles)
- 44 g ethylene oxide (1.0 mole)

After reaction, a viscous oil (720 g), 98 percent yield was recovered (640,000 cps Brookfield viscosity).

The polymer thus formed was of the formula:

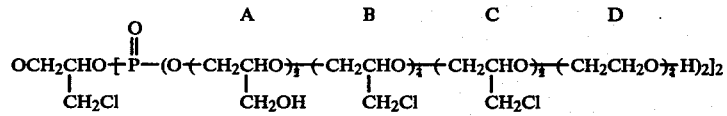

wherein polymeric units A and B were individually in random form and collectively in block copolymeric order with units C and D.

EXAMPLE 9

The reaction conditions of Example 8 were substantially repeated employing the following ingredients added and reacted in the order specified.
- phosphorus pentoxide (71 g, 0.5 mole)
- 400 ml methylene dichloride
- 300 ml 1,4-dioxane
- 246 g 2,3-dibromo-1,4-butenediol (1.0 mole)
- 185 g epichlorohydrin (2.0 moles) + t-BGE (65 g, 0.5 mole)
- 58 g propylene oxide (1.0 mole)
- boron trifluoride etherate (1 ml)

The product obtained was a dark oil (595 g), 98 percent yield (232,000 cps Brookfield viscosity).

The polymer thus formed was of the formula:

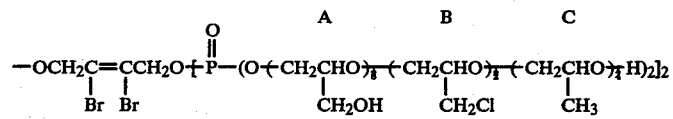

wherein polymer units A and B were in random order and unit C was in block order.

EXAMPLE 10

Polyurethane Formation

The phosphorus-containing polyether polyol of Example 3 was reacted with a polyisocyanate to prepare a polyurethane foam. Properties of the foam were thereafter tested. The reaction and testing were performed according to well-known procedures.

| Formulation | | | |
|---|---|---|---|
| B Side | | A Side | |
| Polyol 1[1] | 72.0 g | 4,4'-diphenyl- | 162 g |
| Polyol 2[2] | 18.0 g | methane- | |
| Example 3 | 10.0 g | diisocyanate[3] | |
| UL-6[4] | 0.1 g | | |
| Polycat ® 8[5] | 2.0 g | | |
| DC-197[6] | 2.0 g | | |

-continued

| Formulation | |
|---|---|
| B Side | A Side |
| Freon 11B[7] 52.5 g | |

[1] Sucrose/Glycerine initiated polypropylene oxide polymer having hydroxyl number of 490
[2] Aminoethylethanolamine initiated polypropylene oxide having a hydroxyl number of 800
[3] Isocyanate index = 130
[4] Tin catalyst commercially available from Union Carbide Corporation
[5] Amine catalyst available commercially from Abbott Laboratories, Inc.
[6] Silicone surfactant available commercially from Dow Corning Corporation
[7] Blowing agent available commercially from E. E. du Pont de Nemours

| Properties | |
|---|---|
| Cream Time (sec) | 21 |
| String Time (sec) | 54 |
| Tack-free Time (sec) | 78 |
| Density lb/ft$^3$ | 1.7 |
| Vertical burn[1] (in/min) | 8.9 |

[1] Measured by igniting a small strip (½" × 3" × ¼") of cured foam in a vertical position in 25% oxygen atmosphere. Burn rate is calculated from observed time for flame to travel 2 inches.

What is claimed is:

1. A phosphorus-containing polyether polyol corresponding to the formula:

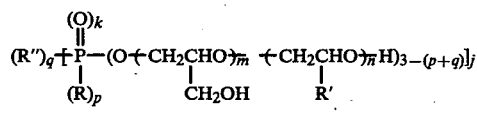

wherein:
R is a monovalent moiety having up to 6 carbons selected from the group consisting of alkyl, phenyl, haloalkyl, halophenyl, alkoxy and haloalkoxy;
R' is $C_{1-6}$ alkyl, $C_{1-6}$ haloalkyl, phenyl, halophenyl, tertiary alkoxy methyl, phenoxy methyl, halophenoxy methyl, or

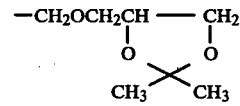

R" is a moiety of valence j having up to 10 carbons selected from the group consisting of R, alkanediyl, alkanetriyl, alkanetetryl, alkenylene, alkylenedioxy and halo-, haloalkyl-, phenyl- or halophenyl-substituted derivatives thereof;
j is an integer from 1 to 4;
k is zero or one;
m is a positive rational number less than about 25;
n is a rational number from zero to about 25; and
p and q are integers independently equal to either zero or 1.

2. The phosphorus-containing polyether polyol of claim 1 wherein R is halomethyl.

3. The phosphorus-containing polyether polyol of claim 2 wherein R is chloromethyl or bromomethyl.

4. The phosphorus-containing polyether polyol of claim 1 having a Brookfield viscosity at 25° C. of less than 500,000 cps.

5. The phosphorus-containing polyether polyol of claim 4 having a Brookfield viscosity at 25° C. of less than 50,000 cps.

6. The phosphorus-containing polyether polyol of claim 1 having a theoretical molecular weight from about 225 to about 2500; a phosphorus content from about 2 percent to about 10 percent by weight; a halogen content from about 10 percent to about 40 percent by weight; and from about 3 to about 9 hydroxyls per molecule.

7. The phosphorus-containing polyether polyol of claim 1 having a theoretical molecular weight from about 400 to about 800; a phosphorus content from about 5 percent to about 10 percent by weight; a halogen content from about 20 percent to about 30 percent by weight; and about 3 to about 5 hydroxyls per molecule.

* * * * *